United States Patent
Kelley et al.

[11] Patent Number: 5,549,750
[45] Date of Patent: Aug. 27, 1996

[54] DISPOSABLE SLIDE HOLDER

[75] Inventors: Thomas F. Kelley, Canton, Mass.; Larry E. Shephard, West Warwick, R.I.; Robert L. Scott, Medfield, Mass.

[73] Assignee: Norfolk Scientific, Inc., Norwood, Mass.

[21] Appl. No.: 270,041

[22] Filed: Jul. 1, 1994

Related U.S. Application Data

[63] Continuation-in-part of Ser. No. 918,491, Jul. 22, 1992, Pat. No. 5,326,398.

[51] Int. Cl.⁶ ..................................... B05C 13/02
[52] U.S. Cl. ...................... 118/55; 118/500; 118/501; 118/52; 118/320
[58] Field of Search ..................... 427/2.11, 2.31, 427/240, 292; 118/501, 52, 55, 500, 56, 320

[56] References Cited

U.S. PATENT DOCUMENTS

| | | | |
|---|---|---|---|
| 3,091,550 | 5/1963 | Doying | 427/387 |
| 3,577,267 | 5/1971 | Preston, Jr. et al. | 117/101 |
| 3,705,048 | 12/1972 | Staunton | 117/3 |
| 3,870,014 | 3/1975 | Buck | 118/52 |
| 4,016,828 | 4/1977 | Maher, Jr. et al. | 118/6 |
| 4,031,852 | 6/1977 | Clarke et al. | 118/52 |
| 4,037,003 | 7/1977 | Maher, Jr. et al. | 427/2 |
| 4,103,643 | 8/1978 | Staunton | 118/50 |
| 4,108,109 | 8/1978 | Barger et al. | 118/52 |
| 4,197,329 | 4/1980 | Holroyd et al. | 427/2 |
| 4,209,548 | 6/1980 | Bacus | 427/2 |
| 4,266,505 | 5/1981 | Bacus | 118/699 |
| 4,280,442 | 7/1981 | Johnson | 118/52 |
| 4,294,866 | 10/1981 | Johnson | 427/2 |
| 4,349,275 | 9/1982 | Ayotte et al. | 356/36 |
| 4,425,372 | 1/1984 | Baldwin | 427/2.31 |
| 4,468,410 | 8/1984 | Zeya | 427/2 |
| 4,574,729 | 3/1986 | Wells | 118/52 |
| 4,576,796 | 3/1986 | McCormick | 118/52 |
| 4,633,804 | 1/1987 | Arii | 118/52 |
| 4,688,513 | 8/1987 | Eberle | 118/52 |
| 4,941,426 | 7/1990 | Sago et al. | 118/52 |
| 5,009,185 | 4/1991 | Stokes et al. | 118/52 |
| 5,326,398 | 7/1994 | Kelley et al. | 118/501 |

*Primary Examiner*—Diana Dudash
*Attorney, Agent, or Firm*—Weingarten, Schurgin, Gagnebin & Hayes

[57] ABSTRACT

A compact slide spinner is disclosed. In the preferred embodiment, the compact slide spinner is used to prepare smears for microscopic evaluation. The spinner incorporates a disposable or reusable slide holder which encases a portion of a slide onto which the material to be smeared is placed. The holder containing the slide is then accelerated by spinning. Specimen fluid not adhering to the slide is contained within the slide holder which is discarded following preparation of the smear. Using this low-cost device, a uniform quality smear is quickly and easily prepared, while reducing the risk that laboratory personnel will be exposed to aerosol borne contagions.

13 Claims, 4 Drawing Sheets

DISPOSABLE SLIDE HOLDER

CROSS-REFERENCE TO RELATED APPLICATIONS

This instant invention is a continuation-in-part of and commonly-assigned U.S. patent application Ser. No. 07/918,491, filed Jul. 22, 1992 (our file STAT-107XX) now U.S. Pat. No. 5,326.398.

FIELD OF THE INVENTION

This invention relates to a device used to prepare smears for microscopic evaluation.

BACKGROUND OF THE INVENTION

Various medical or scientific tests require the preparation of films on transparent slides for microscopic examination. Typically, these films or smears are prepared manually by placing a small amount of fluid, such as blood, cell culture or bone marrow suspension on a microscope slide and pushing or dragging another slide across to form a thin layer. After the slide dries and is treated with a staining solution, a laboratory technician evaluates the film under a microscope. Such manually prepared slides (wedge smears or drag smears) are very technique dependent and produce non-uniform smears or films, with one end too thick, the other end too thin. Additionally, in the case of blood films, the white blood cells are not uniformly distributed across the slide. A superior slide is produced by a slide spinner which consistently distributes a uniform monolayer of cells on a slide.

Prior art slide spinners for preparing blood films disclose a mounting platform for a slide which is able to be rapidly rotated or spun within a containment vessel. Rapid acceleration of the slide causes the blood to be evenly dispersed on the slide. During the short spin cycle, excess blood is flung off the slide into the containment vessel thus forming aerosols.

Use of the prior art devices gives rise to potentially serious health risks related to aerosol borne contagions unless bulky and expensive air filtration systems are employed. In addition to facilitating hazardous aerosol formation, the excess specimen flung off the slides needs to be frequently scrubbed off the containment vessel walls. Even if the containment vessel is lined with absorbent material, it quickly becomes saturated and requires frequent changing. Failure to frequently clean the vessel risks continuing biohazards and creation of a malodor. On occasion slides break, and the glass shards need to be removed along with the residue. These prior art devices thus suffer from aesthetic and biohazard deficits.

Despite having enclosed containment vessels, prior art devices allow for rapid evaporative drying of the film. Thus, care must be taken to ensure spinning is stopped requiring braking systems before the film begins to dry, otherwise there can be artifacts in the film that impair accurate reading. Any buffeting of the cell layer by air turbulence during spinning can also produce artifacts.

Also, while the prior devices may produce a uniform blood film, they do so over the entire slide. No clean area remains for handling and labeling the slide.

Finally, prior art slide spinners have incorporated the use of high power motors with large and heavy, or special purpose, armatures, and commensurately powerful braking systems. This has resulted in spinners which are large and heavy, robbing labs of valuable work space, as well as being mechanically complex, which drove the price of these devices to a point where economic considerations do not favor their use. A practical, compact, cost-effective, safe and effective film preparation device has heretofore been unavailable.

SUMMARY OF THE INVENTION

A compact slide spinner incorporates a disposable slide holder for the preparation of a typically uniform monolayer of cells or particles on a microscope slide. This device consistently produces high quality smears at a lower cost than prior art devices while reducing the production of aerosols and liquid spattering which pose health risks to laboratory technicians.

In accord therewith, a substrate having a surface upon which a monolayer of cells from a liquified specimen is to be prepared, fits within an enclosure designed to hold the surface and retain any of the specimen spun off of the surface. In further accord therewith, the enclosure containing the surface is connected to an acceleration means which accelerates the ensemble of surface and enclosure.

In an illustrative embodiment, the surface is a microscope slide which fits inside an enclosing sheath-style box having openings into which drops of blood or other fluid are introduced upon the slide in consistent locations. The box containing the slide has fittings allowing it to be secured to a platform attached to a motor, which accelerates the platform by spinning it. Following a spin cycle, a slide having a monolayer of cells covering approximately two-thirds of the slide is produced. The enclosing box, containing excess fluid, is then discarded.

One embodiment of the box or enclosure includes an absorbent material disposed within the enclosure. The absorbent material can be a discrete element placed within the enclosure or formed in place from a slurry.

Additionally, a method of forming an absorbent pad within a microscope holder is provided, wherein a slurry including an absorbent material and a liquid carrier is introduced into an enclosure and the liquid carrier is allowed to evaporate. A binder and a disinfectant can be added to the slurry.

BRIEF DESCRIPTION OF THE DRAWINGS

Other features and benefits of the invention can be more clearly understood with reference to the specification and the accompanying drawings in which.

DESCRIPTION OF PREFERRED EMBODIMENTS

Figure 1:
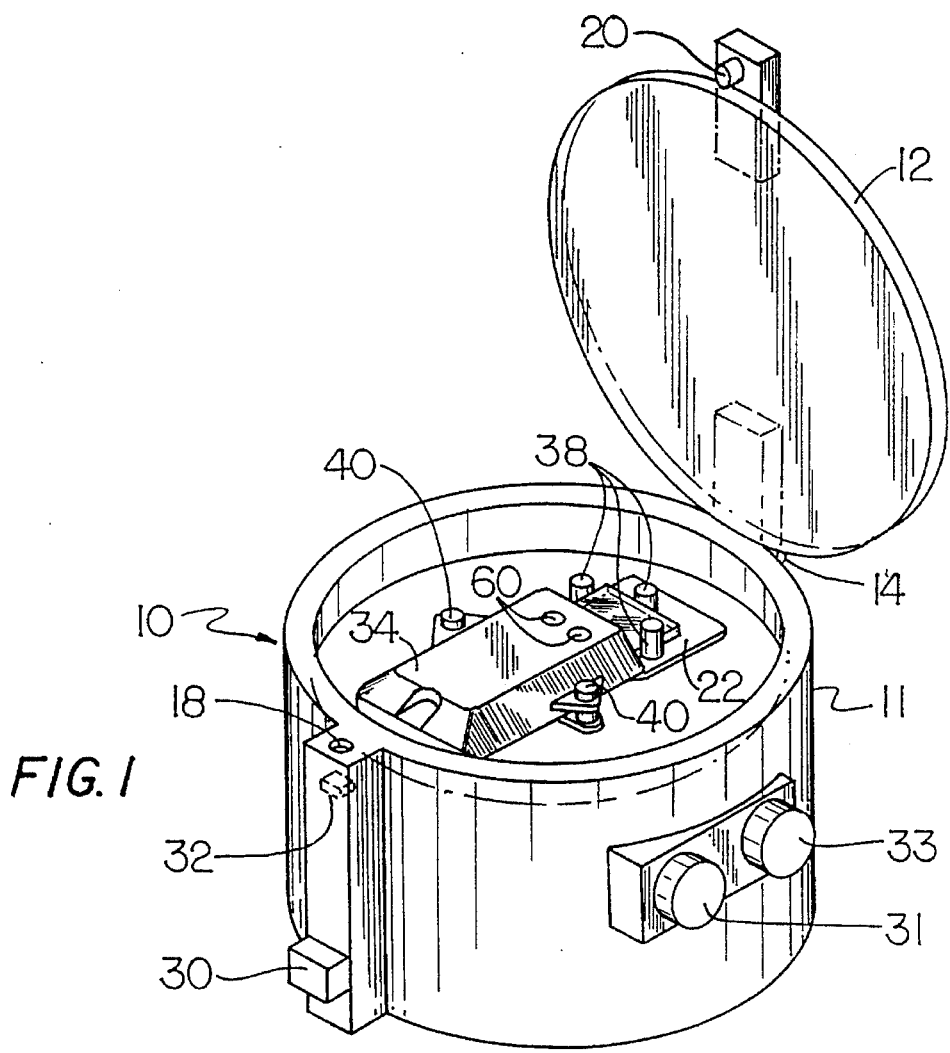
FIG. 1 is a perspective view of the compact slide spinner with mounting platform and slide holder visible.
Figure 1A:
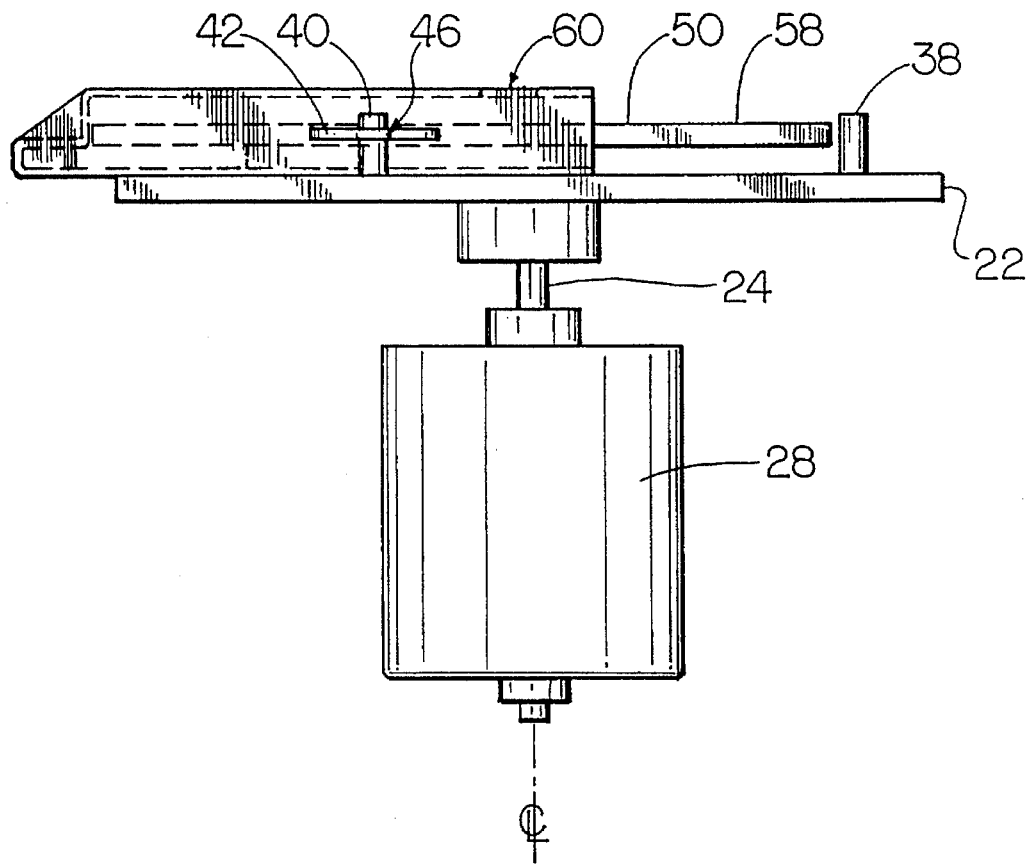
FIG. 1A is a cross-sectional diagrammatical view of a holder and motor with slide inserted.
Figure 3:
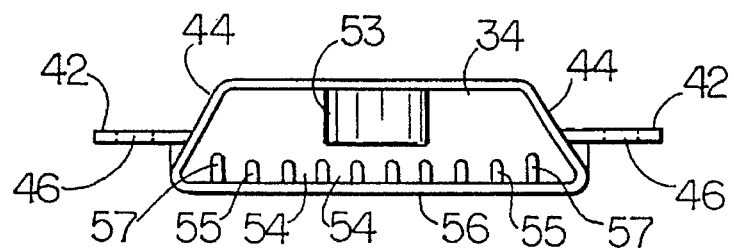
FIGS. 3, 4 and 5 are front sectional, top partially interior and side sectional views of the holder respectively.
Figure 4:
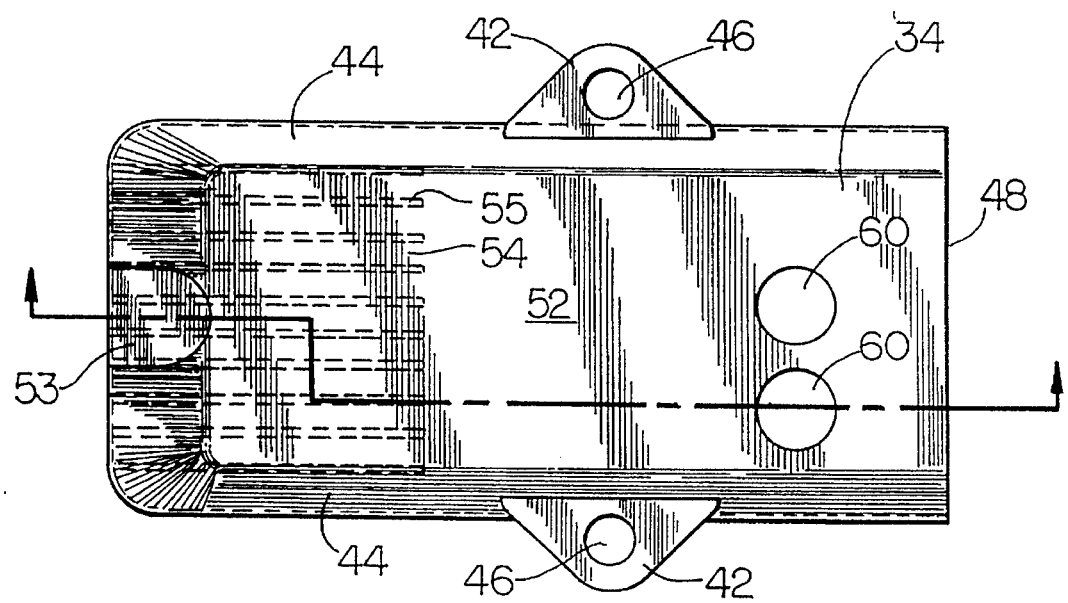
Figure 5:
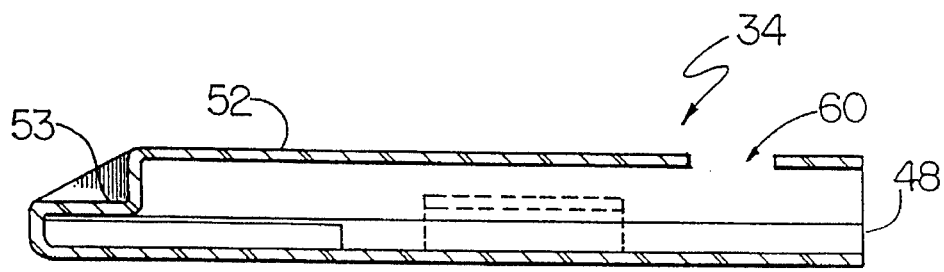

With reference now to FIGS. 1 and 1A, a compact slide spinner 10 is shown with a lid 12 shown open. The lid 12 is attached to the spinner body 11 by a hinge 14 at the rear of the spinner 10. A latch mechanism including a receiving slot 18 and mating pin 20, serves to secure the lid 12 in a closed position.

A mounting platform 22, includes a plurality of posts 38 and 40 disposed on a first surface thereof. The mounting platform is fixed on a drive shaft 24 defining an axis of rotation, which extends into the center of the body 11, and is connected to a motor 28. A power supply (not shown) is used to drive the motor 28 which has a low inertia armature. This small motor 28 allows for correspondingly smaller supporting structures and overall slide spinner 10 size.

The preferred embodiment makes use of electronic controls 31 and 33 to set variables of speeds and times of operation of the motor 28. Also incorporated are a start switch 30 and power interrupt switch 32 in slot 18 to prevent the spinner 10 from being operated with the lid 12 open.

As will be described further in conjunction with FIGS. 2–5 a slide holder 34 includes a pair of mounting tabs 42 having holes 46 therein. The slide holder 34 is disposed on the platform 22 such that the posts 40 are disposed through the holes 46 of the mounting tabs 42 as shown.

It should be noted that here, the mounting tabs 42 (and their respective holes 46 and mounting posts 40) are disposed above and behind the center of gravity of the slide 50 and holder 34 combination. Thus unless a part fails (e.g breaks, fractures or the like) the slide 50 and holder 34 will not dislodge during spinning.

It would be desirable to minimize the rotating mass created by the platform 22, slide holder 34 and slide 50. Ideally, the holder 34 and the slide 50 disposed therein should be spun via a technique which contributes relatively little mass to the rotating assembly. Conventional mounting platforms contribute significant mass especially to the outside, of the spinning assembly which is especially disadvantageous since this makes it more difficult to spin the assembly. Thus a larger, more powerful motor is required to spin the assembly.

In the present invention however, the slide holder 34 and slide 50 are almost suspended, and there is minimum support, and therefore mass, needed under the spinning slide 50 and its holder 34. This is especially advantageous since there is relatively little mass except the slide 50 and holder 34 at the outside or outer rim of the spinning assembly.

While the following describes the preparation of blood films, the spinner 10 may of course be used to provide thin films of other fluid specimens including but not limited to bone marrow suspensions and cell cultures.

Figure 2:
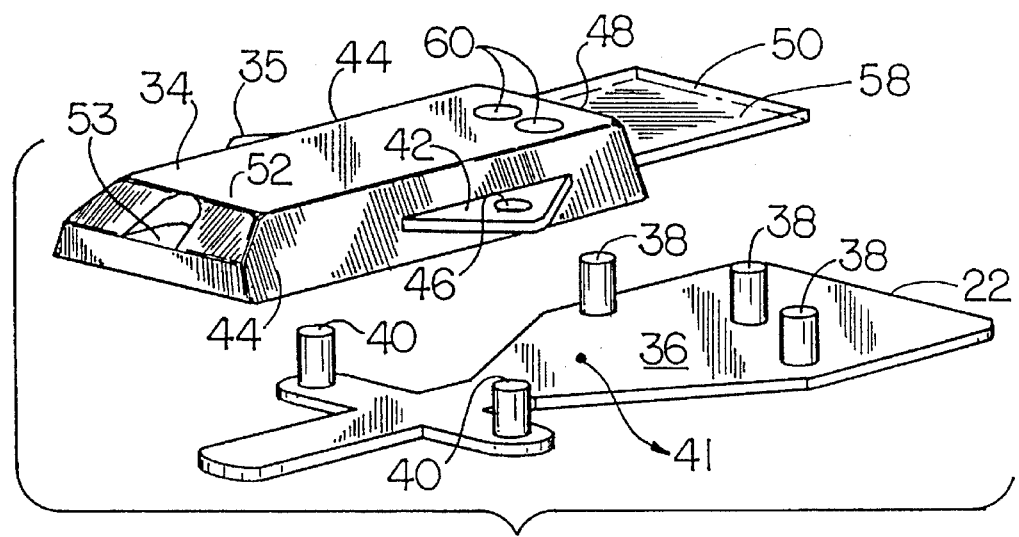
FIG. 2 is a perspective view of the mounting platform and disposable slide holder with slide inserted.

With reference now to FIG. 2, the mounting platform 22 is shown with a disposable slide holder 34. The mounting platform 22 comprises a base 36, three (two lateral and one end) retaining posts 38, two mounting posts 40, and is dimensioned such that with the disposable slide holder 34 and slide in position, the distribution of mass with respect to the center of balance 41 and axis of rotation is roughly equal. It is envisaged, however, that the mounting platform 22 can take any form suitable for the attachment of a container holding or encasing a microscope slide.

With reference to FIGS. 2, 3, 4 and 5, the disposable slide holder 34 approximates a rectangular box in appearance. The holder 34 has two mounting tabs 42, protruding from the sides 44 of the holder 34, each having a hole 46 which corresponds to the spacing of the mounting posts 40 (FIG. 2) and are mounted thereon. The holder 34 could as easily be attached with clips or bands. One end of the holder 34 has an aperture 48 into which a slide 50 (FIG. 2) is introduced. A stop 53 properly locates the slide 50 for consistent operation. The top 52 of the holder 34 has two holes 60 allowing the blood specimen to be placed on an outer third of the slide 50 after the slide 50 is positioned in the holder 34. It is envisaged that blood can be deposited on the slide 50 either before insertion into the holder 34 or via any opening in the holder 34 suitable to insert the blood specimen.

While the slide holder 34 can be as simple as a clear plastic box with an opening, the present invention incorporates several performance enhancing features of particular interest. A series of grooves or channels 54 formed by ribs 55 are located in the bottom 56 of the holder 34 which serve to support and correctly position the slide 50, and to catch and retain blood spun from the slide 50 during spinning. Side ribs (FIG. 3) may be provided that 57 are higher and longer and support the slide 50 over most of its length.

The compact slide spinner 10 (FIG. 1) and disposable slide holder 34 can be better understood by a description of the devices in operation. To prepare a blood smear, a clean slide 50 is inserted into the disposable slide holder 34 via the aperture 48, with a frosted or label edge, if any, remaining outside of the holder 34. The holder 34, with the slide 50 disposed therein, is then placed onto the mounting platform 22 by placing the mounting holes 46 in the tabs 42 on the sides 44 of the slide holder 34, over the mounting posts 40 and pressing down gently until the holder 34 comes to rest flush on top of the mounting platform 22. The labeled end 58 of the slide 50 should come to rest between the retaining posts 38 on the mounting platform 22. The slide 50 is thus positioned normal to the drive shaft 24 as illustrated in FIG. 1A.

Next, a transfer pipette (not shown) is used to place a single drop of specimen fluid such as blood (not shown) for example, through each of the two holes 60 on the top 52 of the slide holder 34 onto slide 50. The two drops of blood (not shown) pool together to ensure uniform coverage on the slide 50. This normally takes one or two seconds. No blood need remain on the outside of the slide holder 34. The slide 50 is then spun immediately after adding the blood.

To start the spin cycle, lid 12 (FIG. 1) of the spinner 10 (FIG. 1) is closed, engaging the latch mechanism (FIG. 1). The operator then activates the start switch 30 (FIG. 1). Then, depending on the previously selected speed setting, the holder 34 is accelerated to 1,500 to 3,000 rpm and stops quickly because of its low inertia. Depending on the previously selected time setting, the entire running time is 0.4 to 3.0 seconds. Despite using a much smaller motor 28 (FIG. 1), and attaining a lower final rotational speed than prior art devices, the compact slide spinner 10 (FIG. 1) achieves the desired result of a uniform monolayer blood smear. By placing the blood specimen farther from the axis of rotation, an effective acceleration rate similar to that undergone in the prior art units using larger motors, attaining up to 6,000 rpm, is achieved.

When the spinner 10 (FIG. 1) comes to a stop the latch mechanism (FIG. 1) can be disengaged, the lid 12 (FIG. 1) is opened, and the slide holder 34 with slide 50 is removed. The slide 50 is then withdrawn and processed in accordance with standard laboratory procedure. The slide holder 34 is subsequently disposed in a manner which reflects the nature of the material contained inside. The holder 34 may thus be low-cost and disposable. Alternatively, under appropriate conditions the holder 34 may be sanitized and reused. When spun in this fashion, the slide 50 will have a blood smear covering approximately two-thirds of one side of the slide 50. The remaining surface area of the slide 50 is free from blood and is suitable for labeling and handling.

Even though the holder 34 is highly effective in reducing aerosol formation, a small amount of liquid blood does remain within the holder 34. Therefore, careless handling and improper disposal of the holder 34 could cause blood to leak from the holder onto a technician or into the environment.

Figure 6:
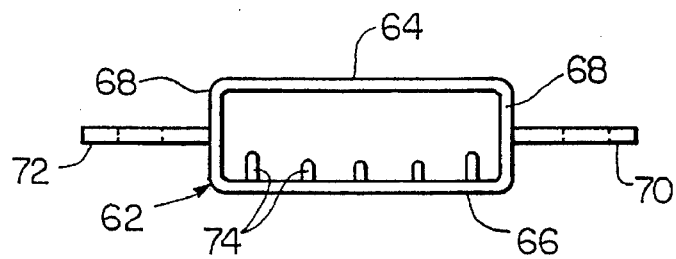
FIGS. 6, 7, and 8 are front sectional, top, and side sectional views of an alternative embodiment of the disposable slide holder.
Figure 7:
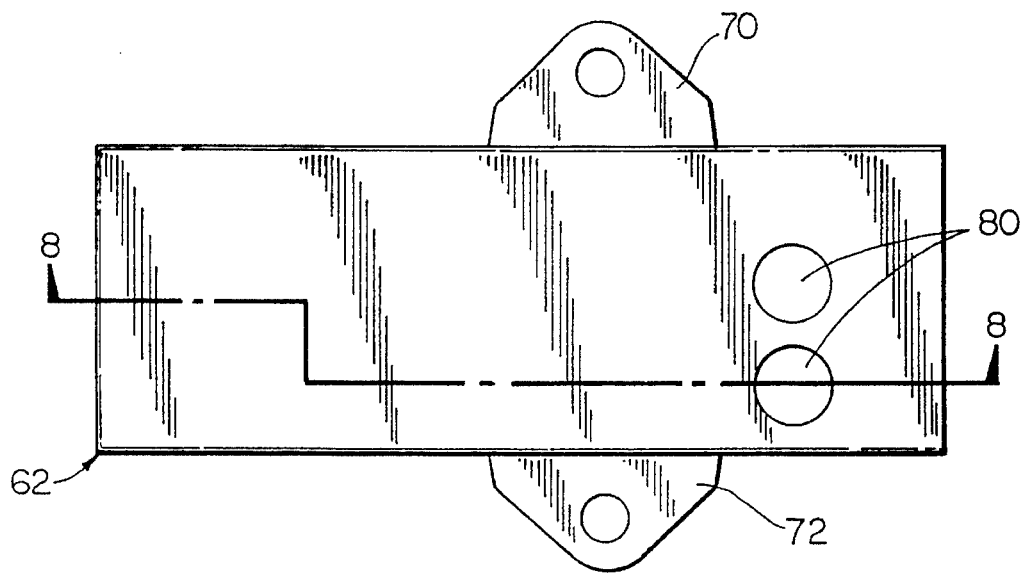
Figure 8:
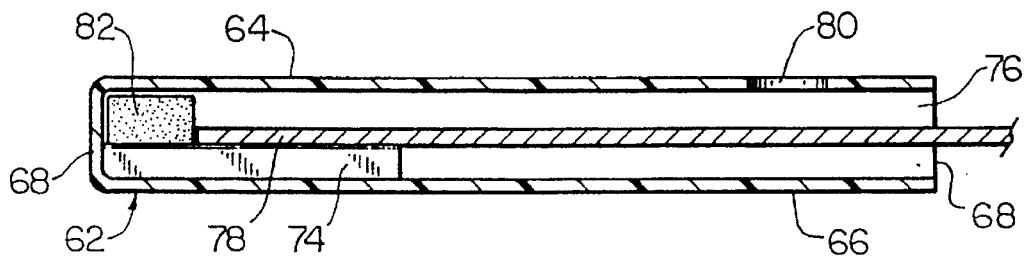

Referring now to FIGS. 6, 7, and 8, an alternative embodiment of the holder is shown which is effective to significantly reduce the possibility of a fluid specimen, such as blood, that has been slung off a substrate, such as a microscope slide, during processing, such as by spinning, from leaking out of the holder.

FIG. 6 is a front sectional view of the alternative holder and it illustrates an enclosure 62 defined by a top 64, a bottom 66, and sides 68 joining the top to the bottom. Also illustrated are mounting tabs 70 and 72, having holes therethrough, for positioning the enclosure 62 on a spinner as described hereinabove. As shown in FIG. 6, ribs 74 can be provided at the bottom of the enclosure which serve not only to strengthen the enclosure, but also to aid in positioning a microscope slide therein. In the exemplary embodiment, the ribs 74 closest to the periphery of the enclosure 62 are the tallest of the ribs and extend the entire length of the enclosure to provide a support surface for the microscope slide. The shorter ribs 74 need not extend the entire length of the enclosure, however, this is not precluded.

Referring to FIG. 8, at least one of the sides 68 includes an opening 76 to receive at least a portion of a microscope slide 78 therethrough. The top 64, which covers the microscope slide 78 includes at least one aperture 80 through which a specimen is introduced into the enclosure 62 and onto the microscope slide 78.

Continuing to refer to FIG. 8, absorbent material 82 is shown disposed within the enclosure 62. In the illustrated embodiment, the absorbent material 82 is positioned within the enclosure 62 proximate the side 68 opposite from the opening 76. In addition to absorbing blood, the absorbent material 82 provides a stop or bumper to position the microscope slide 78 longitudinally within the enclosure. Furthermore, inclusion of an absorbent material into the enclosure removes the temptation to rinse out the enclosure after it has been used for applications where re-use is contraindicated.

The absorbent material 82 can be a simple absorbent pad or a more complex tampon having advanced wicking properties. The pad or tampon can be an element cut from an extrusion or be a molded element adapted to fit within the space allocated within the enclosure 62. Exemplary tampon materials that have excellent wicking properties are sold under the name Transorb by American Filtrona Co. and are constructed of cellulose acetate or polyester. Exemplary molded pads can include those made from a variety of plastics such as polypropylene and polyethylene which have been treated by known techniques to make them hydrophilic. These plastics are manufactured by the Porex company and the Interflow Technologies company.

In an alternative configuration, the absorbent material 82 can be diatomaceous earth, silica gel, hydroxyapatite, or alumina mixed with a binding agent as is known in the art and/or a disinfectant. One contemplated binding agent is a long-chain, noninoic detergent with a carbohydrate such manitol or sorbitol. An exemplary disinfectant is benzethonium chloride.

The absorbent material 82, with or without a binding agent or disinfectant, can be mixed with a carrier liquid to provide a slurry which can then be introduced into the enclosure. If the enclosure is positioned with the opening 76 upward, the slurry collects at the distal end of the enclosure. After the carrier liquid has evaporated, an absorbent pad remains at the distal end of the enclosure in solid form. Since the amount of blood normally spun off of a microscope slide during spinning is small, there is only a very slight chance of any or all of the absorbent material returning to a slurry condition. However, if a binding material is used, this risk can be virtually eliminated.

While the invention has been shown and described with respect to illustrative embodiments thereof, it should be understood that other various changes, omissions and additions in the form and detail thereof will become apparent to those skilled in the art having benefited by the disclosure of the instant invention.

What is claimed is:

1. An enclosure for use in preparing a thin film of a fluid specimen on a microscope slide, comprising:

a top;

a bottom;

a plurality of sides joining said top to said bottom in a fixed relationship, one of said sides including an opening through which at least a portion of said microscope slide is insertable into said enclosure, said top covering said fluid specimen on said microscope slide; and absorbent material disposed within said enclosure.

2. The enclosure of claim 1, wherein said absorbent material is positioned within said enclosure adjacent to a side opposite from said opening.

3. The enclosure of claim 2, wherein said absorbent material limits longitudinal introduction of said microscope slide into said enclosure.

4. The enclosure of claim 1, wherein said absorbent material is a tampon.

5. The enclosure of claim 4, wherein said tampon is fabricated from a material selected from the group consisting of hydrophilic polypropylene, hydrophilic polyethylene, cellulose acetate, and polyester.

6. The enclosure of claim 1, wherein said absorbent material is a material selected from the group consisting of diatomaceous earth, silica gel, hydroxyapatite, and alumina.

7. The enclosure of claim 1, wherein said absorbent material includes a binding agent and a material selected from the group consisting of diatomaceous earth, silica gel, hydroxyapatite, and alumina.

8. An enclosure for use in preparing a thin film of a fluid specimen on a microscope slide, comprising:

a top;

a bottom;

a plurality of sides joining said top to said bottom, at least one of said sides including an opening to receive at least a portion of said microscope slide therethrough, said top covering said fluid specimen on said microscope slide; and absorbent material disposed within said enclosure, said absorbent material including a noninoic detergent with a carbohydrate and a material selected from the group consisting of diatomaceous earth, silica gel, hydroxyapatite, and alumina.

9. The enclosure of claim 1, wherein said absorbent material includes a disinfectant and a material selected from the group consisting of diatomaceous earth, silica gel, hydroxyapatite, and alumina.

10. The enclosure of claim 9, wherein said disinfectant is benzethonium chloride.

11. The enclosure of claim 1, wherein said enclosure includes a plurality of ribs within said enclosure for supporting said microscope slide.

12. The enclosure of claim 1, wherein said top includes an aperture through which said fluid specimen is introduced into said enclosure, said aperture providing vertical access to only a portion of said microscope slide beneath said aperture.

13. The enclosure of claim 1, further including means projecting from one of said plurality of sides for positioning said enclosure on a spinner.

* * * * *